(12) United States Patent
Bange

(10) Patent No.: US 7,749,696 B2
(45) Date of Patent: Jul. 6, 2010

(54) **METHOD AND KIT FOR THE SPECIFIC DETECTION OF *M. TUBERCULOSIS***

(75) Inventor: Franz-Christoph Bange, Hannover (DE)

(73) Assignee: Qiagen Diagnostics GmbH, Hamburg (DE)

( * ) Notice: Subject to any disclaimer, the term of this patent is extended or adjusted under 35 U.S.C. 154(b) by 927 days.

(21) Appl. No.: 10/549,495

(22) PCT Filed: Mar. 19, 2004

(86) PCT No.: PCT/EP2004/002911

§ 371 (c)(1),
(2), (4) Date: Jun. 26, 2006

(87) PCT Pub. No.: WO2004/083459

PCT Pub. Date: Sep. 30, 2004

(65) Prior Publication Data

US 2007/0015157 A1 Jan. 18, 2007

(30) Foreign Application Priority Data

Mar. 20, 2003 (DE) .................. 103 13 791

(51) Int. Cl.
*C12Q 1/68* (2006.01)
(52) U.S. Cl. .................. 435/6; 435/243; 435/253.1; 536/22.1; 536/23.1; 536/23.7; 536/24.1; 536/24.3; 536/24.32; 536/24.33
(58) Field of Classification Search .................. 435/6, 435/243, 253.1; 536/22.1, 23.1, 23.7, 24.1, 536/24.3, 24.32, 24.33
See application file for complete search history.

(56) References Cited

U.S. PATENT DOCUMENTS 6,294,328 B1  9/2001  Fleischmann et al. .......... 435/6

OTHER PUBLICATIONS

GenBank Database, Accession No. AE006997, Fleischmann et al., May 2, 2001.
Cole, S.T., et al., "Deciphering the biology of *Mycobacterium tuberculosis* from the complete genome sequence," *Nature* 393:537-544, Jun. 11, 1998.
Stermann, M., et al., "Polymorphic Nucleotide within the Promoter of Nitrate Reductase (NarGHJI) Is Specific for *Mycobacterium tuberculosis*," *Journal of Clinical Microbiology*, 41(7):3252-3259, Jul. 2003.
Lachnik, J., et al., "Rapid-Cycle PCR and Fluorimetry for Detection of Mycobacteria," *Journal of Clinical Microbiology*, 40(9):3364-3373, Sep. 2002.
Sreevatsan, S., et al., "Restricted structural gene polymorphism in the *Mycobacterium tuberculosis* complex indicates evolutionarily recent global dissemination," *Proceedings of the National Academy of Sciences of USA*, 94(18): 9869-9874, Sep. 1997.

*Primary Examiner*—Rodney P. Swartz
(74) *Attorney, Agent, or Firm*—Seed IP Law Group PLLC

(57) ABSTRACT

The invention relates to a method and system for the specific detection of a *Mycobacterium tuberculosis* (*M. tuberculosis*) in a biological sample, a difference being made, in particular between *M. tuberculosis* and other elements of *M. tuberculosis* complex, i.e., *Mycobacterium bovis* (*M. bovis*), *Mycobacterium bovis* BCG (*M. bovis* BCG), *Mycobacterium africanum* (*M. africanum*) and *Mycobacterium microti* (*M. microti*) based on a SNP in a narGHJI promoter.

48 Claims, 4 Drawing Sheets

Figure 1: Comparison of the narGHJI promotor of *M. tuberculosis* (TB), *M. bovis* (bovis) and *M. bovis* BCG (BCG)

```
    ACGATATTGCGTTGAACGGCACGACGACGCTGCGGGCCTATCGCGTGCATCTGCTTGGCGGCGAACCGCGTGCGCGTGACCACCGGGC
             10        20        30        40        50        60        70        80          TB
1   ........................................................................................  Bovis
1   ........................................................................................  BCG
1   ........................................................................................

GCTGTGCTGGGTGACGGCGGCCGAACTGCACGATGTCGACTGGGTACCAGCCGACCGCGGCTGGATTGCGGACCTGGCGCGAACCCTC
     90       100       110       120       130       140       150       160       170       TB
89  ........................................................................................  Bovis
89  ........................................................................................  BCG
89  ........................................................................................

AACGGGTCCGCCGCAGATGTCCACCGTCGCTGTTAGGAAACCGACGGTGTGGTTGACGGTGGCCGCCGTCAACTTGGTTAGAACAACG
      180       190       200       210       220       230       240       250       260     TB
177 ........................................................................................  Bovis
177 ........................................................................................  BCG
177 ........................................................................................

TGACAAAACGTTAACTTGGGTTTGCATGCCCGTAGCGATCACGATGGTTTTCTGGACGCGTGGCGACAACTTCCGGGCAGGACGCTGA
        270       280       290       300       310       320       330       340       350   TB
265 .......................................T................................................  Bovis
265 ........................................................................................  BCG
265 ........................................................................................

CGCCCATCCATCGAGATACCCGATGTTGACGAGAGGGGTCCCCGACCCGGCGGACCGGGGCTTGACGGGCGCAATGCGGCGCGGCCGG
          360       370       380       390       400       410       420       430       440 TB
353 ........................................................................................  Bovis
353 ........................................................................................  BCG
353 ..........................................................  ............................
                                                                                  -->
    CCAGCCCGTAACGTCCAGCGAGTGCGGTCGCGCGCCGACGGCCCGGCCCCACACCGCTCATGACGAGGAGGTCATCCCGTGACC
            450       460       470       480       490       500       510       520         TB
441 ....................................................................................      Bovis
441 ....................................................................................      BCG
441 ....................................................................................
```

Figure 4: nitrate reductase assay: *M. tuberculosis* wild type and mutants, *M. bovis* and *M. bovis* BCG in comparison
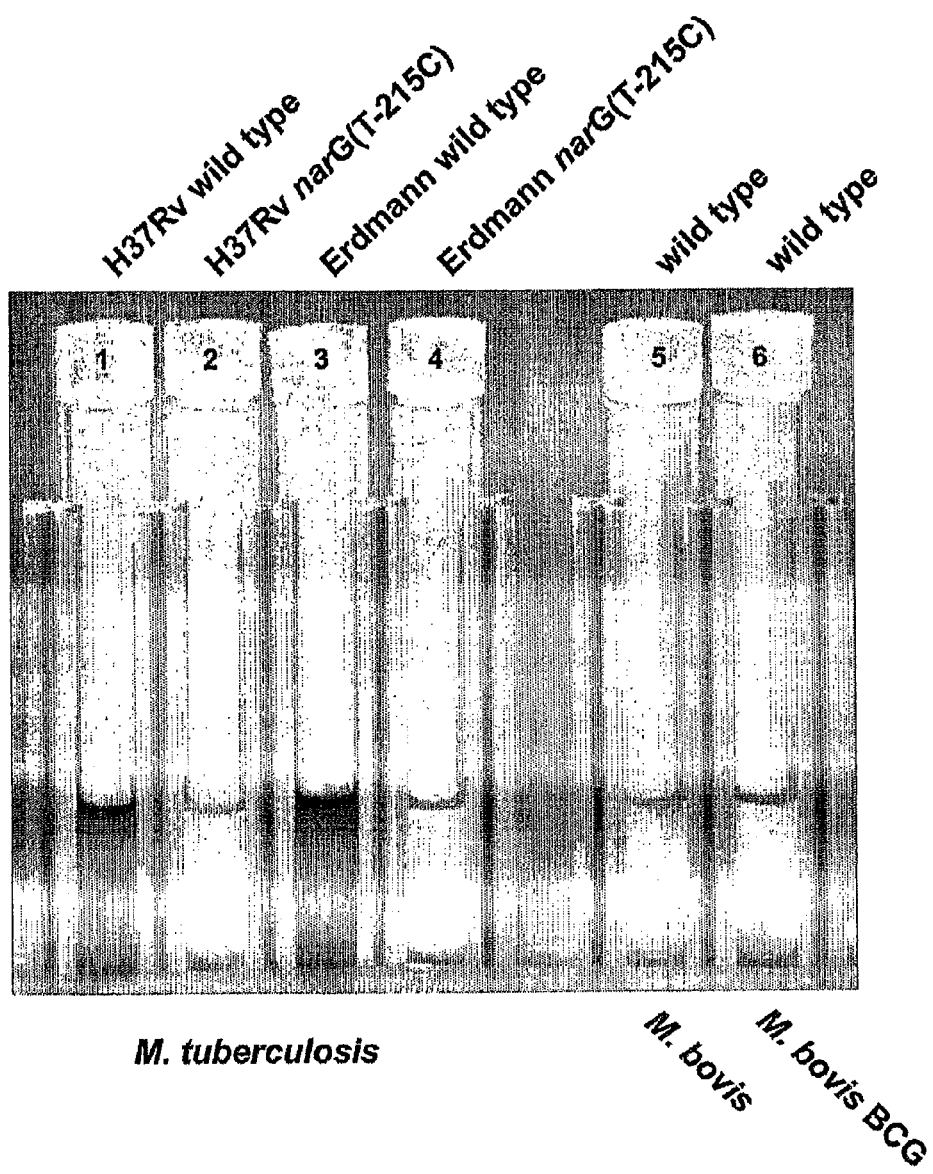

Figure 5: -215 SNP with 150 bp flanking sequences

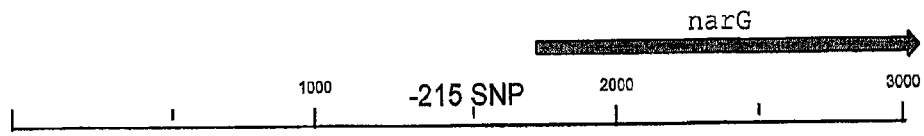

1500 bases upstream and downstream of the -215 SNP ("T") in the promotor of the narGHJI operon:

```
CTCGGGTGTCAAGTTGACGCCGGCGATTACCGCTGTCTACCTCGTCGGCGTTCGGCGGTT      60
GCATGCGGCCGCATTTTCGGTGGTCGTGTTCCTTGCCACCGTCGGCGTGTCGCTACTGGT     120
CGTCGGCGATGAAGCCCGCTACTACTTCACCGACCTGTTGGGCGACGCAGGCCGGGTTGG     180
GCCCATCGCCACCTCCTTCAATCAATCCTGGCGCGGCGCGATTTCCCGGATTCTCGGTCA     240
CGACGCCGGTTTTGGTCCGCTGGTTCTGGCTGCGATCGCCAGTACGGCGGTATTGGCCAT     300
CCTGGCCTGGCGTGCGCTCGACAGGTCCGATCGGCTGGGCAAACTATTGGTGGTCGAGTT     360
GTTCGGCCTGCTGCTCTCGCCGATCTCCTGGACTCACCACTGGGTGTGGCTAGTGCCGCT     420
GATGATCTGGCTGATTGACGGGCCAGCGCGTGAGCGCCCGGGCGCCCGGATTTTGGGCTG     480
GGGCTGGTTGGTGTTGACCATCGTCGGCGTGCCGTGGTTGCTGAGCTTTGCTCAACCGAG     540
CATCTGGCAAATCGGCCGGCCGTGGTATTTGGCCTGGGCCGGTCTGGTCTACGTGGTGGC     600
GACGCTGGCGACCTTGGGCTGGATCGCCGGCCTCCGAGCGTTACGTGCGCATTCGGCCGCG     660
GCGCATGGCCAATTAGGCCCCAAACATTGCGTCGATATCGTGCGCCATCGCAATGTCGTT     720
TTCCGTGATACCACCTACCGCATGCGTAACCAGCGCGAAAGTTACTGTTCGCCAACGGAT     780
ATCGATGTCCGGATGATGATTTACCTCCTCGGCTCGCTCGGCCACCCGGCGTACGGCGTC     840
GATACCGGCCATAAACGTCGGAAACTTGATTGACCTACGCAGGACACCACCGGCGCGCTG     900
CCAGCCGTTGAGGTCGTGCAGTGCGGCGTCGACCTGCTCATCCGTTAACACAGCCATACC     960
TCGACGGTATACCGTCACAGGTCATGCTGAATCAGATCGTGGTTGCCGGAGCCATCGTCC    1020
GCGGTTGCACGGTCTTGGTGGCGCAACGCGTTCGGCCACCGAGCGCGCCGCGCTGGCCCGAGAGC    1080
AACTTCCCGGCGGTAAGGTCGCCGCCGGCGAAACCGAGCGCGCCGCGCTGGCCCGAGAGC    1140
TCGCCGAAGAACTGGGACTCGAGGTCGCCGACCTCGCGGTGGGCGACCGTGTGGGCGACG    1200
ATATTGCGTTGAACGGCACGACGACGCTGCGGGCCTATCGCGTGCATCTGCTTGGCGGCG    1260
AACCGCGTGCGCGTGACCACCGGGCGCTGTGCTGGGTGACGGCGGCCGAACTGCACGATG    1320
TCGACTGGGTACCAGCCGACCGCGGCTGGATTGCGGACCTGGCGCGAACCCTCAACGGGT    1380
CCGCCGCAGATGTCCACCGTCGCTGTTAGGAAACCGACGGTGTGGTTGACGGTGGCCGCC    1440
GTCAACTTGGTTAGAACAACGTGACAAAACGTTAACTTGGGTTTGCATGCCCGTAGCGAT    1500
TACGATGGTTTTCTGGACGCGTGGCGACAACTTCCGGGCAGGACGCTGACGCCCATCCAT    1560
CGAGATACCCGATGTTGACGAGAGGGGTCCCCGACCCGGCGACCGGGGCTTGACGGGCG    1620
CAATGCGGCGCGGCCGGCCAGCCCGTAACGTCCAGCGAGTGCGGTCGCGCGCCGACGGCC    1680
CGGCCCCACACCGCTCATGACGAGGAGGGTCATCCCGTGACCGTTACACCTCACGTCGGT    1740
GGACCGCTCGAAGAGCTGCTGGAGCGCAGCGGGCGCTTCTTCACCCCAGGTGAGTTCTCG    1800
GCCGACCTGCGCACCGTAACCCGGCGCGGCGGCCGCGAAGGTGACGTGTTCTACCGCGAT    1860
CGGTGGAGTCACGACAAAGTGGTCCGATCCACGCACGGAGTCAACTGCACCGGATCCTGC    1920
TCATGGAAGATCTACGTCAAAGACGGGATCATCACCTGGGAAACCCAGCAGACCGACTAC    1980
CCGTCGGTGGGCCCGGACCGGCCCGAATACGAGCCACGAGGTTGTCCCCGTGGCGCGTCG    2040
TTCTCCTGGTACAGCTATTCGCCGACGCGGGTGCGCTATCCGTATGCCCGGGGCGTGCTG    2100
GTTGAGATGTACCGGGAAGCCAAGACCCGCCTGGGCGACCCGGTGCTGGCGTGGGCCGAC    2160
ATTCAGGCGGATCCCGAGCGCAGACGCCGCTATCAACAGGCCCGCGGCAAGGGTGGGCTG    2220
GTCCGGGTGAGCTGGGCCGAGGCCAGCGAGATGGTGGCCGCGCCCACGTGCACACCATC    2280
AAGACATACGGCCGGACCGGGTCGCCGGCTTCTCGCCGATTCCGGCGATGTCAATGGTC    2340
AGCCATGCCGCGGGGTCCCGGTTCGTGGAGCTGATCGGCGGCGTGATGACGTCGTTCTAC    2400
GACTGGTACGCCGACTTGCCGGTGGCCTCGCCGCAGGTGTTCGGCGACCAGACCGACGTG    2460
CCCGAATCCGGCGACTGGTGGGATGCGTCGTATTTGGTCATGTGGGGCTCCAACGTCCCG    2520
ATCACCCGGACGCCCGACGCACATTGGATGGCGGAGGCCCGTTACCGCGGCGCTAAAGTC    2580
GTTGTCGTCAGCCCGGACTACGCCGACAACACCAAGTTCGCCGACGAGTGGGTGCGGTGC    2640
GCCGCCGGTACCGATACCGCGCTGGCGATGGCGATGGGCCACGTGATCCTGTCGGAATGT    2700
TACGTCCGTAACCAGGTTCCGTTCTTTGTCGACTATCGCGCCGCTACACCGACCTGCCG    2760
TTTTTGATCAAGTTGGAAAAGCGGGGCGACCTGCTGGTTCCCGGAAAGTTCTTGACCGCG    2820
GCCGACATTGGTGAAGAAAGTGAGAACGCGGCGTTCAAACCCGCCCTGCTGGATGAGCTT    2880
ACGAATACCGTTGTCGTGCCGCAGGGCTCACTGGGATTCCGTTTCGGTGAGGACGGTGTT    2940
GGGAAGTGGAACCTGGACCTGGGTTCGGTGGTGCCGGCGCTAAGTGTGGAGATGGACAAG    3000
GC
```

METHOD AND KIT FOR THE SPECIFIC DETECTION OF *M. TUBERCULOSIS*

STATEMENT REGARDING SEQUENCE LISTING

The Sequence Listing associated with this application is provided in text format in lieu of a paper copy, and is hereby incorporated by reference into the specification. The name of the text file containing the Sequence Listing is 770036_402USPC_SEQUENCE_LISTING.txt. The text file is 7 KB, was created on Feb. 27, 2009, and is being submitted electronically via EFS-Web.

The present invention relates to methods and means for the specific detection of *Mycobacterium tuberculosis* (*M. tuberculosis*) in a biological sample, the distinction between *M. tuberculosis* and the other members of the so-called *M. tuberculosis* complex, i.e. *Mycobacterium bovis* (*M. bovis*) *Mycobacterium bovis* BCG (*M. bovis* BCG), *Mycobacterium africanum* (*M. africanum*) and *Mycobacterium microti* (*M. microti*), in particular, being achieved.

At present, approximately 2 thousand million people worldwide have been infected with the pathogen of tuberculosis, *M. tuberculosis,* 8 million succumbing to tuberculosis every year. Of those suffering from tuberculosis, 3 million die every year. Consequently, tuberculosis is at present the bacterial infectious disease which most frequently leads to death. Because of the seriousness of the disease, tuberculosis is notifiable immediately after diagnosis in most industrialized nations not least in order to prevent spreading among the population as quickly as possible. In the last few years, an increased occurrence of tuberculosis has been observed both in the developing countries and in the industrialized nations, cases of death caused by it having been registered regularly above all in the case of immunosuppressed HIV patients. However, not only because of the general risk to large parts of the world population but also because of the meanwhile epidemic-type occurrence of multiply resistant bacteria strains (MDRTB) within or outside of hospitals, a rapid and clear-cut diagnosis for the detection of *M. tuberculosis* is required.

In man, tuberculosis is caused worldwide practically exclusively by the human tuberculosis pathogen *Mycobacterium tuberculosis*. The following need to be delimited from this: *Mycobacterium bovis* (*M. bovis*), the pathogen of cattle tuberculosis, *Mycobacterium bovis* (BCG), an attenuated strain of *M. bovis* which is used for immunization against tuberculosis and *Mycobacterium africanum* (*M. africanum*) and *Mycobacterium microti* (*M. microti*). As a result of their close relationship, all the above-mentioned species are combined in the so-called *M. tuberculosis* complex. From this, the so-called non-tuberculous mycobacteria need to be delimited. There are at present approximately 100 different species of these, at least 30 species of which occur in human material such as saliva, faeces, urine etc. and are capable in some cases of leading also to infection and/or illnesses. The aim of the present efforts in the field of mycobacteria diagnosis is consequently not only the provision of mycobacteria tests which make it possible to recognize a mycobacteria infection within the shortest possible time at an early infection stage but also to specifically identify the members of the *M. tuberculosis* complex and to distinguish at the same time between *M. tuberculosis* and other members of the *M. tuberculosis* complex.

An identification of the members of the *M. tuberculosis* complex and the distinction between *M. tuberculosis* and the other members of the *M. tuberculosis* complex can normally be effected by testing the nitrate reductase activity and niacin accumulation of the mycobacteria (e.g. Metchock B. G. et al. In: Manual of Clinical Microbiology. ASM Press, Washington D.C., 1999: 399-437). In this respect, *M. tuberculosis* is characterized, in comparison with the other members of the *M. tuberculosis* complex, by an increased nitrate reductase activity. In order to carry out the nitrate reductase test, however, the cultivation of the mycobacteria strains isolated from the clinical material, consequently in particular tuberculous pathogen strains, is above all necessary in the laboratory, which, normally, is possible only in laboratories specially equipped for the cultivation of highly infectious pathogens and, because of the slow growth of the pathogens, takes several weeks. The availability of such tests in clinical routine diagnosis is consequently associated with a high expenditure in terms of laboratory technology and finance.

All the detection methods existing so far are regarded as being unsatisfactory and consequently requiring improvement. No method suitable for clinical routine use which stands out in particular as a result of its simple application and by means of which it is possible to detect the members of the *M. tuberculosis* complex specifically in clinical material such as saliva, bronchial lavage, gastric juice, urine, faeces, bone marrow, blood or in biopsies and to distinguish simultaneously *M. tuberculosis* from the other members of the *M. tuberculosis* complex has so far become known from the state of the art.

It is known that the use of the real time PCR ("rapid cycle PCR") which is equipped with an air-tempered system and consequently exhibits considerably lower transition times compared with a conventional PCR, for example, leads to a substantially reduced time up to the detection of e.g. mycobacteria by amplification of the isolated genetic material of the mycobacterium (Chapin and Lauderdale, J. Clin. Microbiol. (1997) 35:2157-2159). In addition, fluorimetric measurements represent a rapid and sensitive method for the detection of amplified gene fragments when using colour-labelled hybridization probes, in particular within the framework of rapid cycle PCR. So far however, it has not been possible to provide a (real time) PCR test by means of which the members of the *M. tuberculosis* complex are specifically detected and, simultaneously, *M. tuberculosis* is distinguished from the other members of the *M. tuberculosis* complex.

Against this background, it is the object of the present invention to provide in particular improved methods and means which permit essentially a particularly rapid and simultaneously specific detection of members of the *M. tuberculosis* complex and by means of which it is simultaneously possible to distinguish *M. tuberculosis* from the other members of the *M. tuberculosis* complex.

According to the invention, the object is achieved by the methods according to claims 1 to 11, primer and primer pairs according to claims 12-17, hybridization probes and hybridization probe pairs according to claims 19 to 28, by the use according to claims 18 and 29 and in particular by kits according to claims 30 to 35 and/or the subject matter of claims 36 of 51.

The present invention relates in particular to a method for the specific detection of *M. tuberculosis* in a biological sample in which method a nucleic acid amplification method is carried out using primers which are suitable for amplifying a DNA segment from the sequence shown in SEQ ID NO: 1 which sequence comprises a segment from the region of the narGHJI nitrate reductase operon, the DNA segment comprising position −215 in the 5' to 3' direction of reading upstream of the translation start codon GTG of the narGHJI nitrate reductase operon and in the case of which the polymorphism specific for *M. tuberculosis* is detected in position −215 in the 5' to 3' direction of reading upstream of the translation start codon GTG of the narGHJI nitrate reductase operon.

NarGHJI nitrate reductase operon should be understood to mean, according to the invention, a nucleic acid sequence, including the regulatory sequences, in particular including its promoter, which encodes narGHJI nitrate reductase. The polymorphism specific for *M. tuberculosis* is an individual nucleotide exchange (T→C), i.e. an SNP (single nucleotide polymorphism) specific in comparison with the nucleic acid sequences of the other members of the *M. tuberculosis* complex, i.e. *M. bovis* BCG, *M. africanum* and *M. microti.*

According to an embodiment of the invention, microbial DNA is extracted, in a first step, from the sample which preferably contains clinical material and, in a further step, at least one DNA fragment of the nitrate reductase operon of mycobacteria, i.e. the narGHJI operon which encodes nitrate reductase is amplified from the extracted DNA, the amplified DNA fragment—or one of the amplified DNA fragments (insofar as representatives of several mycobacteria strains are present in the biological sample)—containing a target region (target sequence) which exhibits at least one DNA polymorphism specific for *M. tuberculosis.*

In a further step, the specific hybridization of the at least one amplified DNA fragment is detected with at least one hybridization probe, i.e. oligonucleotide, the hybridization probe comprising a nucleotide sequence which is preferably selected from the group consisting of the nucleotide sequence represented in SEQ ID No: 5, the complementary sequence to SEQ ID NO: 5, the nucleotide sequence represented in SEQ ID NO: 6 and the complementary sequence to SEQ ID NO: 6, the specific detection of *M. tuberculosis* vis-à-vis other members of the *M. tuberculosis* complex, i.e. *M. bovis*, BCG, *M. africanum* and *M. microti* taking place by analysis of the melting temperature of the specific hybridization of the hybridization probe with the amplified DNA fragment of the narGHJI operon, i.e. by melting curve analysis. According to a particular embodiment, the probe/probes exhibits/exhibit the above-mentioned nucleotide sequence/nucleotide sequences. According to a particular embodiment, the above-mentioned hybridization probes are combined with the anchor probe according to SEQ ID NO: 4 or the nucleotide sequence complementary therewith.

According to the invention, the at least one *M. tuberculosis*-specific DNA polymorphism of the narGHJI operon is preferably located in position −215 in the 5' to 3' direction of reading upstream of the translation start codon GTG of the narGHJI operon, i.e. in the promoter region, hereinafter called narGHJI promoter. Types of *M. tuberculosis* formed by mutation which exhibit this polymorphism (T in comparison with C in the case of the other members of the *M. tuberculosis* complex) in the narGHJI promoter are included even if this is not positioned in position −215 but at a position which differs with respect to the translation start codon GTG of the narGHJI operon.

Surprisingly enough, it has been found within the framework of the present invention that, instead of the 215$^{th}$ nucleotide in the 5' to 3' direction of reading upstream of the translation start codon GTG of the narGHJI operon, i.e. in position −215 of the narGHJI promoter, a thymine base is to be found in the case of *M. tuberculosis* whereas a cytosine base is present in the case of the other members of the *M. tuberculosis* complex in particular *M. africanum, M. microti, M. bovis* and *M. bovis* (BCG) (see, FIG. 1). This single base polymorphism is specific for *M. tuberculosis* and is, above all, stable as confirmed by a comparative investigation into more than 100 *M. tuberculosis* strains worldwide. Moreover, it has been found unexpectedly that this one nucleotide polymorphism is responsible for the different reactions in the nitrate reductase test of *M. tuberculosis* in comparison with the other members of the *M. tuberculosis* complex (see, example 4).

According to the invention, at least one primer, in particular at least one primer pair is preferably used for the amplification of the DNA fragment of the narGHJI operon, the primers containing, i.e. comprising, in particular, however, consisting of, i.e. exhibiting, the nucleotide sequence represented in SEQ ID NO: 2 and/or the nucleotide sequence represented in SEQ ID NO: 3. Preferably, according to the invention, the at least one pair of labelled hybridization probes preferably used for the specific hybridization of the amplified DNA fragment contains, in particular it consists of, nucleotide sequences selected from the group of the nucleotide sequence pairs of the nucleotide sequences represented in SEQ ID NO: 4 and in SEQ ID NO: 5, the pair of complementary sequences of SEQ ID NO: 4 and SEQ ID NO: 5, the nucleotide sequences represented in SEQ ID NO: 4 and in SEQ ID NO: 6 and the pair of complementary sequences of SEQ ID NO: 4 and SEQ ID NO: 6.

A clear-cut detection of a tuberculous infection by pathogen strains of the type *M. tuberculosis*, i.e. in particular the strains of *M. tuberculosis* H37v (ATCC 25618) and *M. tuberculosis* Erdmann (ATCC 35801) and other clinical strains takes place, according to the invention, preferably by the analysis of the melting temperatures of the specific hybridization of a labelled hybridization probe pair with the nucleotide sequences SEQ ID NO: 4 and SEQ ID NO: 5 or the pair of complementary sequences with a narGHJI promoter region, specifically for *M. tuberculosis*. In this respect, *M. tuberculosis* stands out by melting temperatures of in particular less than 61° C., preferably less than 59° C., particularly preferably of approximately 57° C. In comparison, the pathogen strains of the mycobacteria types *M. africanum, M. microti, M. bovis* and *M. bovis* BCG to be distinguished from *M. tuberculosis*, possess, when the labelled hybridization probe pair SEQ ID NO: 4/SEQ ID NO: 5 is used, melting temperatures of, in particular, more than 59° C., preferably of more than 61° C., particularly preferably of more than 63° C.

Depending on the hybridization conditions actually prevailing, e.g. on the buffer composition, the design of the probes as labelled probes or by modification of the nucleotide sequence of the probes, (usually slight) changes to the absolute melting temperature may arise; obviously, all those methods in the case of which such modified melting temperatures occur represent preferred embodiments of methods according to the invention presented here.

In a further variant, the clear-cut detection of a tuberculous infection by pathogen strains of the type of *M. tuberculosis*, i.e. in particular the strains of *M. tuberculosis* H37v (ATCC 25618) and *M. tuberculosis* Erdmann (ATCC 35801) as well as further clinical strains takes place according to the invention preferably by the analysis of the melting temperatures of the specific hybridization of a labelled hybridization probe pair with the nucleotide sequences SEQ ID NO: 4 and SEQ ID NO: 6 or the pair of the complementary sequences with a narGHJI promoter region specific for *M. tuberculosis* (see, Table 1). The pathogen strains of the type of *M. tuberculosis* are characterized in this respect by melting temperatures of in particular more than 58° C., preferably more than 60° C., particularly preferably of approximately 62° C. In comparison, the pathogen strains of *M. africanum, M. microti, M. bovis* and *M. bovis* BCG, when the labelled hybridization probe pair SEQ ID NO: 4/SEQ ID NO: 6 is used, possess melting temperatures of in particular less than 62° C., preferably less than 60° C., particularly preferably of approximately 58° C.

The nucleic acid amplification according to the invention can take place, for example, by Polymerase Chain Reaction (PCR), Nucleic Acid Sequence Based Amplification (NASBA), Strand Displacement Amplification (SDA) or Ligase Chain Reaction (LCR). In addition, any desired further nucleic acid amplification methods can obviously be considered as suitable.

Moreover, it has, surprisingly, been found that when using at least one primer, in particular one primer pair comprising the nucleotide sequence represented in SEQ ID NO: 2 and/or comprising the nucleotide sequence represented in SEQ ID NO: 3 for the amplification of at least one DNA fragment of the promoter region of the narGHJI nitrate reductase operon of mycobacteria, the amplification takes place exclusively in the case of the pathogen strains of the *M. tuberculosis* complex, i.e. leading to an amplification product. In the case of non-tuberculous pathogens or non-mycobacterial pathogens, however, no amplification takes place which means that no corresponding amplification product is obtained. By using the primers according to the invention, the clear-cut distinction between the pathogen strains *M. tuberculosis* and the other pathogen strains of the *M. tuberculosis* complex as well as vis-à-vis non-tuberculous mycobacteria and non-mycobacteria, for example actinomycetes, pathogens of the genus *Bacillus, Staphylococcus, Listeria, Enterococus* and *Proteus, E. coli, Salmonella, Shigella, Klebsiella* or *Pseudomonas* or fungal pathogens is possible particularly advantageously.

In a preferred embodiment of the above-mentioned methods, the amplification of the DNA fragments by Polymerase Chain Reaction (PCR) is carried out. In a particularly preferred embodiment, the PCR is a real time PCR (rapid cycle PCR).

The detection of the polymorphism specific for *M. tuberculosis* can take place, according to the invention, by the specific hybridization of one or several probes.

In the real time PCR method, it is possible to observe the multiplication of the PCR products in real time, amplification cycle by amplification cycle. Particularly preferably, the amplification is carried out in LightCycler™ system from Roche Molecular Biochemicals which is an embodiment of real time PCR. For this purpose, hybridization probes which bind specifically to the desired PCR amplification products, in particular, are also added to the PCR starting mixture, apart from polymerase, the nucleotides, the buffer solutions and the primers. In this connection, two sequence-specific oligonucleotide probes are used in particular which are labelled with different dyes. The sequences of the hybridization probe pairs labelled according to the invention are selected in such a way that they hybridize to the target sequence of the amplified DNA fragment in such a way that the 3' end of the one probe is situated close to 5' end of the other probe as a result of which the two dyes are brought into direct vicinity to each other; preferably, the distance between the two probes is between 1 and 5 nucleotides. In particular, a fluorescence resonance energy transfer (FRET; see, e.g. Heid et al, Genome Res. 6 (1996) 986-994) between the two dyes of the hybridization probes and consequently a shift in the fluorescence spectrum occurs, the degree of fluorescence in this wave length region being a function of the quantity of detected DNA. The detection can take place according to the method according to WO 00/58505, for example.

According to the invention, the FRET system also provides for quantitative measurements of the quantity of amplified DNA fragments. The hybridization probes selected according to the invention can bind quantitatively, i.e. stoichiometrically, to the amplified fragments. In this respect, the quantitative hybridization is dependent in particular on the temperature and the degree of homology of the oligonucleotide probes used with the detected sequence on the amplified DNA fragment.

In a preferred embodiment, the fluorimetric detection of specific DNA sequences in the amplified fragments is carried out after amplification of the fragments by conventional PCR. In an embodiment which is particularly preferred, the fluorimetric detection is carried out in a rapid cycle PCR during the amplification reactions in which, for example, the increase in DNA produced can be monitored as an increase in the fluorescence signal.

In a preferred embodiment of the method according to the invention, the specific detection of the amplified DNA fragments takes place on completion of the amplification reaction, wherein, within the framework of a melting curve analysis, the temperature being modified, preferably increased continuously, following the hybridization of the hybridization probe pair, preferably of a FRET pair, to the region to be detected, and the fluorescence emitted simultaneously as a function of the temperature being measured. In this way, a melting temperature is determined at which the hybridization probes, in particular the FRET pair used, just no longer hybridize to the region, to be detected, of the amplified DNA fragment. The essential aspect of a melting curve analysis consists of the fact that, in the case of the occurrence of mismatches between the hybridization probe pair used and the target region on the amplified DNA fragment, a reduction of the melting point measured takes place. Using hybridization probes, in particular an FRET pair, the regions of DNA fragments are identified according to the invention in this way whose sequences differ only very slightly from each other by one or several point mutations in the nucleotide sequence.

In connection with the present invention, the terms "segment", "region", "fragment", "target region" or "flanking region" should be understood to mean at least one coherent area on a linear, strand-type deoxy or ribonucleic acid molecule, i.e. DNA or RNA, which, measured in the number of nucleotides of this molecule, consists, in the 5' to 3' direction of reading downstream and/or upstream of a certain numbered nucleotide of the molecule, i.e. a certain position, preferably of 200, 100, 50, 40, 30, 20, 10, 5, 4, 3 or 2 nucleotides of the molecule.

A DNA segment amplified according to the invention preferably has, in addition to the sequence to which the primer binds, a length of at least 1 and maximum 500 nucleotides, preferably maximum 300 and particularly preferably maximum 155 nucleotides. Individual length values which are within the above-mentioned region, are expressly included, i.e. 2, 3, 4, 5 . . . , 497, 498 and 499. The amplified DNA segment can obviously be longer, shorter segments in practice being probably preferred.

According to an embodiment of the invention, the primer pair used for the method has at least one of the sequences with SEQ ID NO: 2 and SEQ ID NO: 3 or the complementary sequences, thereof.

In an embodiment of the invention, the detection of the polymorphism specific for *M. tuberculosis* takes place with at least one pair of labelled hybridization probes, one probe being labelled at its 3' end and the other probe at its 5' end and the probes binding specifically to the amplificate in such a way that a fluorescence resonance energy transfer (FRET) is made possible.

In a preferred embodiment, the probe pair exhibits the sequences with the SEQ ID NO: 4 and 5 or the complementary sequences thereof and/or the sequences with the SEQ ID NO: 4 and 6 or the complementary sequences thereof.

The subject matter of the invention is, moreover, a method for the joint detection of pathogens of the *M. tuberculosis* complex in clinical materials, the presence of an amplification product of the narGHJI promoter region being detected in particular by at least one hybridization probe specific for the amplified DNA fragment, preferably by the above-described method and pathogen strains of the *M. tuberculosis* complex thus being detected vis-à-vis non-tuberculous pathogens and/or vis-à-vis non-mycobacteria. In an alternative variant, the occurrence of an amplification product is detected in a manner known as such, in particular by electrophoretic methods. In this connection, the method of the present invention can be part of a comprehensive detection method in which further, preferably pathogen-specific (type specific or species specific) detections are carried out by nucleic acid amplification corresponding to specific sequence segments in parallel batches or in the same reaction batch, in particular in connection with a multiplex PCR.

An essential advantage of the method according to the invention consists of the fact that, in a detection method for the diagnosis of mycobacteria infections, both an existing infection with *M. tuberculosis* can be clearly, accurately and in particular simultaneously recognized, preferably in a single routine diagnostic batch vis-à-vis other microbial infections, an infection with *M. tuberculosis* vis-à-vis non-tuberculous infections and in infection with *M. tuberculosis* vis-à-vis other members of the *M. tuberculosis* complex. A further essential advantage of the method according to the invention is that, the mycobacteria strain of the type of *M. tuberculosis* can be detected additionally, in particular simultaneously and in a clear-cut manner and this type can be identified individually. The detection methods according to the invention consequently allow in particular a clear-cut and accurate early recognition of tuberculosis and the clear-cut and accurate early recognition of the type-dependence to *M. tuberculosis* of isolated pathogen strains of the *M. tuberculosis* complex. This permits particularly advantageously a rapid and controlled therapy of the infected organism.

Essentially, the method according to the invention is used in routine diagnosis and essentially in routine laboratories. Carrying out the method in specially equipped safety laboratories of complex design to cultivate highly infectious pathogen strains is not necessary. For this reason, the method according to the invention can be made available to a wide range of users.

In connection with the present invention, clinical materials should be understood to mean essentially clinical samples, i.e. patient material such as saliva, bronchial lavage, gastric juice, urine, faeces, liquor, bone marrow, blood but also biopsies, in particular aspirate biopsies such as e.g. from the lymph nodes in the neck. However, clinical material should also be understood to mean culture isolates e.g. from liquid culture, in particular from liquid culture for the selective cultivation of acid resistant rod cells, in particular from patient material.

Preferably, the microbial DNA is extracted from the clinical material in a manner known as such, in particular by means of DNA preparation kits such as the QIAmp™ DNA Mini Kit from Qiagen.

Preferably, the sample according to the invention is selected from the group of clinical samples selected consisting of saliva, bronchial lavage, gastric juice, urine, faeces, liquor, bone marrow, blood and biopsies.

The present invention also relates to the primers, primer pairs, probes and probe pairs required for the execution of the above-mentioned methods.

A primer pair which is suitable for the amplification of a DNA segment from the sequence shown in SEQ ID NO: 1 which comprises a segment from the area of the narGHJI nitrate reductase operon is preferred according to the invention, the DNA segment comprising position −215 in the 5' to 3' direction of reading upstream of the translation start codon GTG of the narGHJI nitrate reductase operon.

According to the invention, the primer pair is preferably used for the amplification of a DNA fragment with a DNA polymorphism of the narGHJI gene specific for pathogen strains of the type *M. tuberculosis* from the extracted DNA with a length of 155 bp, in the case of which the forward primer comprises and/or exhibits the nucleotide sequences according to SEQ ID NO: 2 and the reverse primer the nucleotide sequence according to SEQ ID NO: 3. A further subject matter of the invention consequently also consists of at least one oligonucleotide primer, preferably at least one oligonucleotide primer pair, for the amplification of a DNA fragment of the *M. tuberculosis*-specific promoter region of the narGHJI nitrate reductase gene containing, in particular consisting of, nucleic acid molecules with nucleotide sequences represented in SEQ ID NO: 2 and/or SEQ ID NO: 2 or comprising these nucleotide sequences.

In a preferred embodiment, at least one primer of a primer pair exhibits the sequence indicated in SEQ ID NO: 2 or the complementary sequence thereof or comprises it.

In a further preferred embodiment, at least one primer of a primer pair exhibits the sequence indicated in SEQ ID NO: 3 or the complementary sequence thereof or comprises it.

In a particularly preferred embodiment, the primers of a primer pair exhibit the sequences indicated in SEQ ID NO: 2 and those indicated in SEQ ID NO: 3 or the complementary sequences thereof.

Primers according to the invention may exhibit the sequence indicated in SEQ ID NO: 2 or the complementary sequence thereof or the sequence indicated in SEQ ID NO: 3 or the complementary sequence thereof.

An embodiment of the invention relates to the use of one the above-mentioned primers or primer pairs for the specific detection of *M. tuberculosis*, i.e. by amplification of *M. tuberculosis* DNA contained in a biological sample and the specific detection of the amplificate obtained.

The invention preferably relates also to primers and/or primer pairs for the amplification of the DNA fragments used according to the invention which, compared with the above-mentioned primers according to the invention comprising the nucleotide sequences represented in SEQ ID NO: 2 and 3, degenerated, mutated or modified sequences or fragments thereof in each case, which hybridize with the nucleotide sequence concerned represented in SEQ ID NO: 2 and 3 from which they are derived, a degree of homology existing in each case preferably over the entire length of the sequence of at least 92%, preferably of at least 97%, particularly preferably of at least 98% compared with the original nucleotide sequence. In this respect, the derived fragments have a sequence length in each case which is preferably maximum 98% of the length the nucleotide sequence, particularly preferably maximum approximately 95%, maximum approximately 90%, maximum approximately 75%, maximum approximately 50% or maximum approximately 25%. Particularly preferably, the derived fragment is maximum 10, maximum 5, 4, 3 or 2 nucleotides or one nucleotide shorter compared with the original nucleotide sequence.

In connection with the present invention, the term "modified sequence" or "modified nucleotide sequence" should be understood to be a nucleic acid sequence which, by exchange, inversion, deletion or addition of at least one nucleotide, including an unusual or synthetic nucleotide, differs from its original sequence in at least one nucleotide, preferably in two nucleotides. In this connection, the term "modified" should be understood to mean a characteristic which relates to a modified nucleotide sequence.

In connection with the present invention, the wordings "primer which comprises the nucleotide sequence" or "hybridization probe which comprises the nucleotide sequence" or similar should be understood to mean that the primers and probes concerned exhibit the nucleotide sequences, i.e. consist of the specifically mentioned nucleotide sequences alone. The wording should also be understood to mean that the primers and probes concerned consist, if necessary, of at least one further additional sequence, apart from the nucleotide sequences mentioned in concrete terms. This additional sequence flanks the nucleotide sequences mentioned in concrete terms and has a sequence length which amounts to preferably maximum approximately 100% of the length of the nucleotide sequence mentioned in concrete terms, particularly preferably maximum approximately 75%, maximum approximately 50%, maximum approximately 25%, maximum approximately 10%, maximum approximately 5% or maximum approximately 2%. Particularly preferably, the additional sequence has a length of 10 to 5 nucleotides, of 4, 3, 2 nucleotides or it consists of a single nucleotide.

A hybridization probe according to the invention is a probe which is suitable for the specific detection of the polymorphism specific for *M. tuberculosis* which is located in position −215 in the 5' to 3' direction of reading upstream of the translation start codon GTG of the narGHJI nitrate reductase operon.

The hybridization probe pair according to the invention is a probe pair which is suitable for the specific detection of the polymorphism specific for *M. tuberculosis* which is located in position −215 in the 5' to 3' direction of reading upstream of the translation start codon GTG of the narGHJI nitrate reductase operon.

A further subject matter of the invention also consists of at least one oligonucleotide hybridization probe which hybridizes specifically with an *M. tuberculosis*-specific promoter region of the narGHJI nitrate reductase operon which contains, in particular consists of, the nucleic acid molecule with the nucleotide sequence represented in SEQ ID NO: 5 or with the complementary sequence thereof. A further subject matter of the invention also consists of at least one oligonucleotide hybridization probe pair which contains, in particular consists of, the nucleic acid molecules with the nucleotide sequences represented in SEQ ID NO: 4 and in SEQ ID NO: 5 or with the complementary sequences thereof.

A further subject matter of the invention also consists of a further or alternative oligonucleotide hybridization probe which hybridizes specifically with an *M. tuberculosis*-specific promoter region of the narGHJI nitrate reductase operon which contains, in particular consists of, the nucleic acid molecule with the nucleotide sequence represented in SEQ ID NO: 6 or with the complementary sequence thereof. A further subject matter of the invention also consists of at least one oligonucleotide hybridization probe pair which contains, in particular consists of, the nucleic acid molecules with the nucleotide sequences represented in SEQ ID NO: 4 and in SEQ ID NO: 6 or with the complementary sequences thereof.

In a particularly preferred embodiment, at least one probe of a hybridization probe pair exhibits the sequence indicated in SEQ ID NO: 4 or the complementary sequence thereof or the sequence indicated in SEQ ID NO: 5 or the complementary sequence thereof or the sequence indicated in SEQ ID NO: 6 or the complementary sequence thereof.

In a particularly preferred embodiment, the probes of a hybridization probe pair exhibit the sequences indicated in sequence SEQ ID NO: 4 and SEQ ID NO: 5 or the complementary sequences thereof or the sequences indicated in sequence SEQ ID NO: 4 and SEQ ID NO: 6 or the complementary sequences thereof.

Hybridization probes according to the invention may exhibit the sequence indicated in SEQ ID NO: 4 or the complementary sequence thereof or the sequence indicated in SEQ ID NO: 5 or the complementary sequence thereof or the sequence indicated in SEQ ID NO: 6 or the complementary sequence thereof.

In a manner preferred according to the invention, the detection of the DNA fragments is carried out with the above-mentioned hybridization probes which are executed as FRET pairs, i.e. labelled, a hybridization probe partner being executed as donor component="anchor probe" which is associated preferably at the 3' terminal nucleotide with a dye, preferably a fluorescence dye, particularly preferably with fluorescein. According to the invention, the hybridization probes comprising the nucleotide sequence represented in SEQ ID NO: 4 or the complementary sequence thereof are provided preferably as anchor probes.

The hybridization probe partner, which is different in each case, of the hybridization probe pair is executed as acceptor component=sensor probe which is preferably associated at the 5' terminal nucleotide with a further dye, preferably with a rhodamine derivative. According to the invention, the hybridization probes comprising the nucleotide sequences represented in SEQ ID NO: 5, 6 or the complementary sequences thereof in each case are preferably provided as sensor probes. In preferred variants of the above-mentioned embodiments, the rhodamine derivative is LightCycler-Red 640®, in further preferred variants of the above-mentioned embodiment the rhodamine derivative is LightCycler-Red 705®, in further preferred variants of the above-mentioned embodiment the rhodamine derivative is Cy5. Particularly preferably, the labelled sensor probes used for the type-specific detection of *M. tuberculosis* according to the invention carry the dye LightCycler-Red 640 or LightCycler-Red 705®.

A further embodiment of the invention relates to the use of one of the hybridization probes described above or one of the hybridization probe pairs described above for the specific detection of *M. tuberculosis*.

Obviously, the present invention also comprises means such as e.g. kits (devices) for carrying out a method according to the invention.

In one embodiment, a kit comprises at least one primer pair which is suitable for the amplification of a DNA segment from the sequence shown in SEQ ID NO: 1 which comprises a segment from the area of the narGHJI nitrate reductase operon, the DNA segment comprising position −215 in the 5' to 3' direction of reading upstream of the translation start codon GTG of the narGHJI nitrate reductase operon and/or at least one hybridization probe or one hybridization probe pair which is suitable for the specific detection of the polymorphism specific for *M. tuberculosis* which is located at position −215 in the 5' to 3' direction of reading upstream of the translation start codon GTG of the narGHJI nitrate reductase operon.

In a particularly preferred embodiment, the kit comprises at least one primer pair in the case of which the primers exhibit the sequences indicated in SEQ ID NO: 2 and SEQ ID NO: 3 or the complementary sequences thereof.

In a further preferred embodiment, the kit comprises at least one hybridization probe pair in which the probes exhibit SEQ ID NO: 4 and SEQ ID NO: 5 or the complementary sequences thereof or SEQ ID NO: 4 and SEQ ID NO: 6 or the complementary sequences thereof.

In a particularly preferred embodiment, the kit comprises both a primer pair in the case of which the primers exhibit the sequences indicated in SEQ ID NO: 2 and SEQ ID NO: 3 or the complementary sequences thereof as well as a hybridization probe pair in which the probes exhibit the SEQ ID NO: 4 and SEQ ID NO: 5 or the complementary sequences thereof or the SEQ ID NO: 4 and SEQ ID NO: 6 or the complementary sequences thereof.

In a further embodiment, the kit additionally comprises further equipment, reagents and/or auxiliary agents necessary for carrying out a nucleic acid amplification and/or detection reaction of the amplificate.

A further subject matter of the invention also consists of the use of at least one M. tuberculosis-specific DNA polymorphism in the promoter region of the narGHJI nitrate reductase operon of mycobacteria, in particular in position −215 in the 5' to 3' direction of reading upstream of the translation start codon GTG of the narGHJI operon for the specific detection of an infection with M. tuberculosis. In a particularly preferred variant, this genome segment is characterized in that it contains, in particular consists of, the nucleic acid sequence represented in SEQ ID NO: 1 or the complementary sequence. Preferably, the use according to the invention takes place in at least one PCR batch with subsequent or simultaneous hybridization, e.g. in a rapid cycle PCR or in a method of conventional hybridization known as such of DNA sequencing, in particular in a capillary sequencing device, namely allel-specific PCR, OLA ("Oligonucleotide Ligation Assay"), SSCP ("Single Strand Conformation Polymorphism") or Denatured Gradient Gel Electrophoresis (DGGE). Alternative methods for amplification consist, apart from PCR, for example of the known methods of NASBA, SDA or LCR.

The invention will be explained in further detail by way of the appended sequence protocol which contains SEQ ID NOs: 1 to 6, by way of FIGS. 1 to 5 and by way of examples 1 to 4.

SEQ ID NO: 1—region in the area of the narGHJI operon which comprises the polymorphism specific for M. tuberculosis in position −215 in the narGHJI promoter.

SEQ ID NO: 2—forward primer for the amplification of a 155 by fragment of the narGHJI promoter of mycobacteria containing a DNA polymorphism specific for M. tuberculosis, SEQ ID NO: 3—reverse primer to SEQ ID NO: 2;

SEQ ID NO: 4—hybridization probe (antisense), in particular anchor probe and donor component of a probe pair for the detection of the type-specific region of the narGHJI promoter of mycobacteria;

SEQ ID NO: 5—hybridization probe (antisense), in particular sensor probe and acceptor component of a probe pair for the detection of the type-specific region of the narGHJI promoter of mycobacteria;

SEQ ID NO: 6—hybridization probe (antisense), in particular sensor probe and acceptor component of a probe pair for the detection of the type-specific region of the narGHJI promoter of mycobacteria;

DESCRIPTION OF THE FIGURES

FIG. 4—shows a diagnostic nitrate reductase test with specifically produced T-215C mutants of M. tuberculosis, the corresponding Wild types and M. bovis and M. bovis BCG. The red colouration (dark) by the diazonium dye formed from naphtyl amide and sulphanyl acid indicates the nitrate accumulation in the medium: the Wild types of M. tuberculosis alone exhibit a nitrate accumulation; the T-215C mutants thereof posses (again) the M. bovis phenotype.

FIG. 5—shows an area of the narG gene (SEQ ID NO: 1) which exhibits the nucleotide polymorphism specific for M. tuberculosis (T) in position −215 upstream of the translation start codon GTG.

EXAMPLES

Example 1

DNA Isolation a) From Clinical Material

Figure 1:
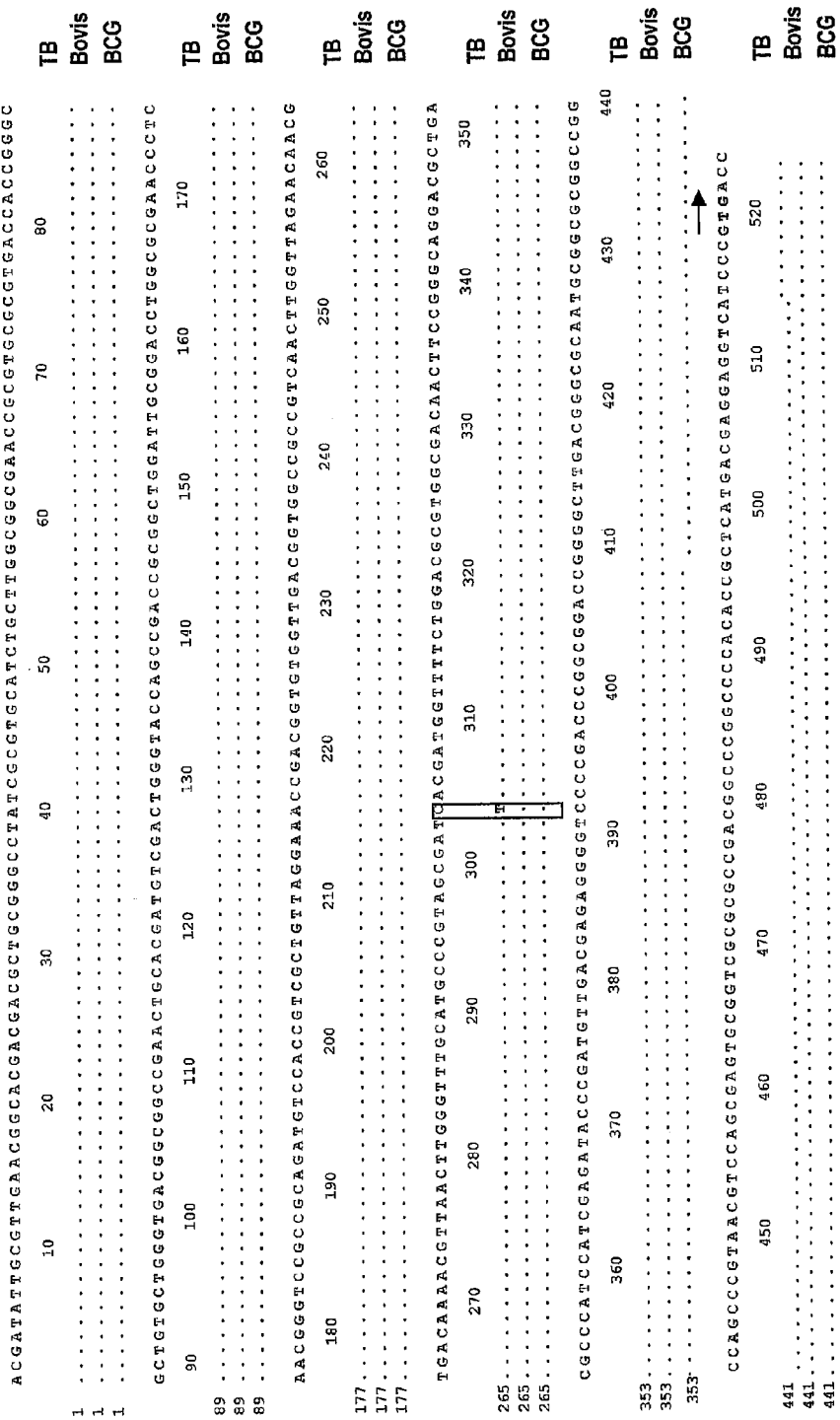
FIG. 1—shows an alignment of the narGHJI promoter regions of M. tuberculosis, M. bovis and M. bovis BCG (SEQ ID NOs: 7-9). The labelled area shows the nucleotide polymorphism specific for M. tuberculosis ("T").

Microbial DNA is purified, i.e. extracted, from clinical samples consisting of saliva, bronchial lavage, gastric juice, urine, faeces, liquor, bone marrow, blood or aspirate biopsies in the known way, e.g. by means of a QIAmp™ DNA Mini Kit (Qiagen, Hillden, Germany).

b) From Culture Isolates

Cultures from microorganisms, to be diagnosed, from patient samples are cultivated in an automated cell culture system BACTEC™ MGIT™ (Becton, Dickinson and Company Diagnostic Systems, USA) in liquid cultures under conditions which promote the cultivation of acid-resistant cell rods, in particular of mycobacteria. From the positive cultures, the microbial DNA is obtained for example by means of mechanical disruption. The microbial DNA is extracted in the known way, for example by means of a QIAmp™ DNA Mini Kit (Qiagen, Hilden, Germany) from the culture isolates and, if necessary, aliquoted.

Example 2

PCR Amplification

For amplification in optimized LightCycler™ PCR, a batch containing the ready-for-use obtainable mixture of "LightCycler FastStart DNA Master Hybridization Probes" (Catalogue No. 239272, Roche Molecular Biochemicals) is chosen.

The following reaction mixture is produced for the Light-Cycler reaction:

FastSart™ Taq polymerase
reaction buffer
desoxynucleoside triphosphate mixture (dNTP)

3 mmol/l MgCl$_2$ (end concentration)
primer, per primer: 19 pmol corresponding to 1.1 µmol/l end concentration
oligonucleotide FRET probe pair
per probe: 2 pmol corresponding to 100 nmol/l end concentration This reaction mixture is transferred by pulse centrifuging into the glass capillary of the LightCycler system and the amplification is carried out according to the "Hot Start" principle after initial denaturing at 95° C. for 10 minutes with the following steps.

1. Denaturing at 95° C. for 3 seconds
2. Primer hybridization at temperatures of 68° C. to 62° C. for 2 seconds ("touch down annealing")
3. Polymerization at 72° C. for 40 seconds Steps 1 to 3 are carried out 50 times in total, the hybridization for the first 5 cycles taking place in step 2 at 68° C. and during the subsequent 6 cycles the temperature being reduced to 62° C. in steps of 1° C. per cycle and for the remaining cycles at 62° C. The rate of temperature change is 20° C. per second in all steps.

For the amplification of the region of the narGHJI promoter containing the DNA polymorphism specific for *M. tuberculosis*, the primer with the nucleotide sequence SEQ ID NO: 2 is used as forward primer and the primer with the nucleotide sequence SEQ ID NO: 3 as reverse primer. 155 by fragments of the narGHJI promoter are amplified. It is further found that the use of these primers leads to an amplification product only in the case of pathogen strains of the *M. tuberculosis* complex but not in the case of non-tuberculous pathogens or non-mycobacterial pathogens. For this reason, the use of the primers with the nucleotide sequence SEQ ID NO: 2 and/or SEQ ID NO: 3 also allows the clear-cut distinction to be made between pathogens of the type of the *M. tuberculosis* complex vis-à-vis non-tuberculous types and vis-à-vis pathogens of non-mycobacteria.

Example 3

Detection and Melting Curve Analysis

To detect the amplified fragments, FRET-labelled hybridization probe pairs used in the reaction mixture (see, example 2) are used, one hybridization probe partner (SEQ ID NO: 4) being associated as donor component at the 3' terminal nucleotide with fluorescein and the hybridization probe partner which is different in each case (SEQ ID NO: 5 or 6) is associated as acceptor component on the 5' terminal nucleotide with LightCycler Red™ 640. The melting curve analysis which takes place during the detection with the hybridization probes immediately after the last amplification cycle begins with the denaturization of the amplified fragments at 95° C. for 30 seconds, followed by a hybridization with the above-mentioned FRET pairs at 38° C. for 30 seconds. To determine the melting curves of hybridization, the temperature is subsequently increased continuously from 38° C. to 80° C. at a rate of 0.2° C. per second, the fluorescence emitted by the conjugated FRET pairs being recorded continuously. The fluorescence dies out regularly as soon as at least one hybridization probe partner melts. To evaluate the fluorescence signal, the LightCycler "run profile" program in version 3.5.3 is used, the amplification of the F2 and F3 channel of the photometric detector of the LightCycler system being automatically adjusted.

For the specific hybridization of the region of narGHJI promoter containing the DNA polymorphism specific for *M. tuberculosis*, the FRET-labelled hybridization probe pair with the nucleotide sequences SEQ ID NO: 4/SEQ ID NO: 5 is used. As an alternative, the FRET-labelled hybridization probe pair with the nucleotide sequences SEQ ID NO: 4/SEQ ID NO: 6 is used for the specific hybridization of the region of the narGHJI promoter containing the DNA polymorphism specific for *M. tuberculosis*.

Figure 2:
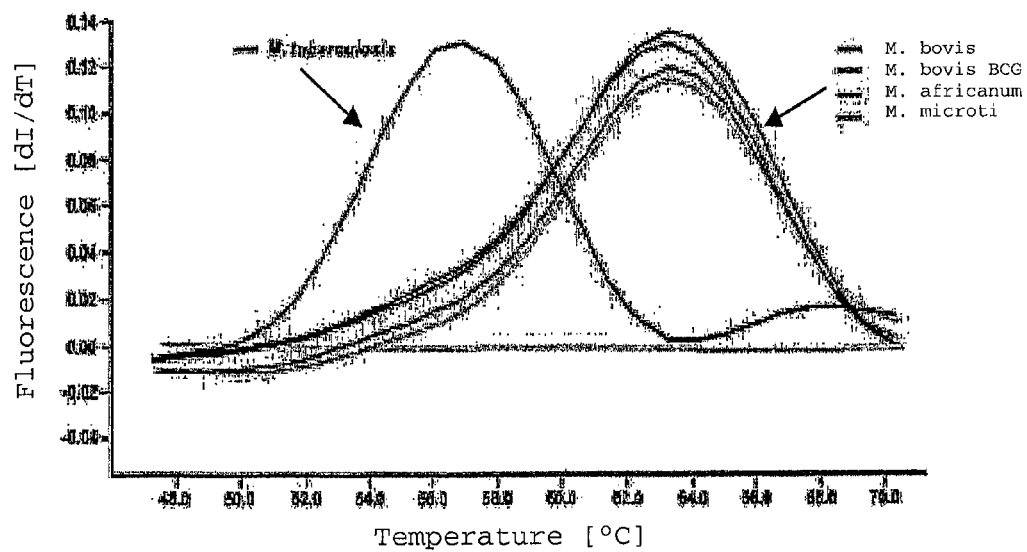
FIG. 2—shows melting curves of the hybridization of the specific hybridization probe pair with SEQ ID NO: 4/SEQ ID NO: 5 with the region, specific for M. tuberculosis, in the amplified 155 by fragment of the narGHJI promoter.
Figure 3:
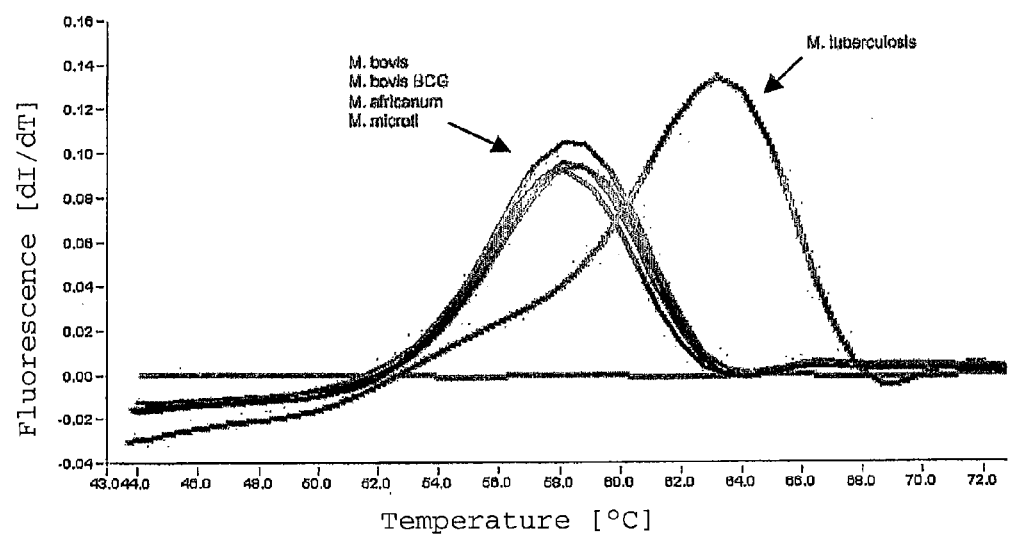
FIG. 3—shows melting curves of the hybridization of the specific hybridization probe pair with SEQ ID NO: 4/SEQ ID NO: 6 with the region, specific for M. tuberculosis, in the amplified 155 by fragment of the narGHJI promoter.

FIGS. 2 and 3 and Table 1 show the results of the melting curve analysis.

Example 4

Comparison of the Method According to the Invention with the Conventional Nitrate Reductase Test In comparative tests, different samples containing *M. tuberculosis*, *M. bovis* and *M. bovis* BCG were subjected to the method according to the invention and to the conventional nitrate reductase test (FIG. 4).

The following samples were used, the sample numbers corresponding to the numbering in FIG. 4:

*M. tuberculosis*:
1. H37Rv Wild type;
2. H37Rv narG (T-215C)
3. Erdmann Wild type;
4. Erdmann narG (T-15C)

*M. bovis*:
5. Wild type

*M. bovis* BCG
6. Wild type

Samples no. 1 and 3 tested positively using the method according to the invention (see, Examples 3 and 4), i.e. *M. tuberculosis* was specifically detected, a clear-cut distinction being possible between the mycobacteria strains no. 5 and 6. Samples 2 and 4, in the case of which the sequence encoding T in position −215 was modified by gene technology in such a way that it encodes C, exhibited lower values in the melting curve and comparable values in the case of samples 5 and 6 containing *M. bovis* and *M. bovis* BCG.

The biochemical test, the nitrate reductase test, confirmed the result, the non-modified *M. tuberculosis* samples no. 1 and 3 testing positively whereas no colour reaction was observed in the case of samples containing *M. bovis* and *M. bovis* BCG and the samples containing *M. tuberculosis* strains modified by T→C exchange by gene technology in position −215, which confirms the significance of the polymorphism in position −215 for the detection method according to the invention.

TABLE 1

| | | Melting temperature [° C.] of the hybridisation probes specific for | |
|---|---|---|---|
| Type | Strain | M. tuberculosis Probe SEQ ID NO: 6 Target region: narGHJI pro. | M. tuberculosis Probe SEQ ID NO: 5 Target region: narGHJI pro. |
| M. tuberculosis | H37v ATCC 25618 | 62.3° | 56.8° |
| | Erdmann ATCC 35801 | 62.2° | 57.0° |
| | Clinical strains (n = 33) | 62.2° (SD = 0.29) | 56.9° (SD = 0.36) |
| M. africanum | Clinical strains (n = 3) | 57.9° (SD = 0.14) | 63.4° (SD = 0.21) |
| M. microti | Clinical strains (n = 2) | 57.0° (SD = 0.14) | 63.20° (SD = 0.28) |

TABLE 1-continued

| | | Melting temperature [° C.] of the hybridisation probes specific for | |
|---|---|---|---|
| Type | Strain | M. tuberculosis Probe SEQ ID NO: 6 Target region: narGHJI pro. | M. tuberculosis Probe SEQ ID NO: 5 Target region: narGHJI pro. |
| M. bovis | ATCC 19210 | 58.2° | 63.1° |
| | Clinical strains (n = 12) | 58.0° (SD = 0.22) | 63.2° (SD = 0.30) |
| M. bovis BCG | Pasteur ATCC 35734 | 57.9° | 63.6° |
| | Copenhagen ATCC 27290 | 58.0° | 63.5° |
| | Moreau ATCC 35736 | 58.2° | 63.7° |
| | Tice ATCC 35743 | 58.2° | 63.5° |
| | Connaught ATCC 35745 | 58.2° | 63.7° |
| | Clinical strains (n = 4) | 57.9° (SD = 0.14) | 63.2° (SD = 0.26) |

The invention claimed is:

1. A method for determining the presence or absence of *Mycobacterium tuberculosis* (*M. tuberculosis*) in a biological sample, comprising (a) performing nucleic acid amplification in the presence of the nucleic acids from the biological sample and a primer pair suitable for amplifying a DNA segment comprising a region of SEQ ID NO:1 that encompasses position −215, in the 5' to 3' direction of reading, upstream of the translation start codon GTG of the narGHJI nitrate reductase operon, and (b) determining in the amplification product of step (a), the presence or absence of the polymorphism specific for *M. tuberculosis* in position −215, wherein the polymorphism specific for *M. tuberculosis* in position −215 is thymine (T), and wherein the presence of the polymorphism indicates the presence of *M. tuberculosis* in the biological sample, and the absence of the polymorphism indicates the absence of *M. tuberculosis* in the biological sample.

2. The method according to claim 1, wherein step (a) is carried out by polymerase chain reaction (PCR), nucleic acid sequence based amplification (NASBA), strand displacement amplification (SDA) or ligase chain reaction (LCR).

3. The method according to claim 2, wherein the PCR is a real time PCR.

4. The method according to any one of claims 1 to 3, wherein step (b) is carried out by hybridization of one or several probes.

5. The method according to any one of claims 1 to 3, wherein the DNA segment of step (a) has a length of 1 to 500 nucleotides.

6. The method according to any one of claims 1 to 3, wherein the DNA segment of step (a) has a length of 1 to 300 nucleotides.

7. The method according to any one of claims 1 to 3, wherein the DNA segment of step (a) has a length of 1 to 155 nucleotides.

8. The method according to any one of claims 1 to 3, wherein one primer of the primer pair of step (a) comprises SEQ ID NO:2 or SEQ ID NO:3.

9. The method according to any one of claims 1 to 3, wherein step (b) is carried out by means of at least one pair of labeled hybridization probes, one probe being labeled at its 3' end and the other probe being labeled at its 5' end, and the probes binding specifically to the DNA segment of step (a) in such a way that a fluorescence resonance energy transfer (FRET) is made possible.

10. The method according to claim 9, wherein one probe of the probe pair comprises SEQ ID NO:4 and the other probe comprises SEQ ID NO:5; one probe of the probe pair comprises the complementary sequence of SEQ ID NO:4, and the other probe comprises the complementary sequence of SEQ ID NO:5; one probe of the probe pair comprises SEQ ID NO:4 and the other probe comprises SEQ ID NO:6; or one probe of the probe pair comprises the complementary sequence of SEQ ID NO:4 and the other probe comprises the complementary sequence of SEQ ID NO:6.

11. The method according to any one of claims 1 to 3, wherein the sample is a clinical sample selected from the group consisting of saliva, bronchial lavage, gastric juice, urine, faeces, liquor, bone marrow, blood and biopsies.

12. A hybridization probe for detecting the polymorphism specific for *M. tuberculosis* located in position −215 in the 5' to 3' direction of reading upstream of the translation start codon GTG of the narGHJI nitrate reductase operon, wherein the polymorphism specific for *M. tuberculosis* in position −215 is thymine (T).

13. A hybridization probe pair for detecting the polymorphism specific for *M. tuberculosis* located in position −215 in the 5' to 3' direction of reading upstream of the translation start codon GTG of the narGHJI nitrate reductase operon, wherein the polymorphism specific for *M. tuberculosis* in position −215 is thymine (T).

14. The hybridization probe pair according to claim 13, wherein one probe of the probe pair comprises SEQ ID NO:4 or the complementary sequence thereof.

15. The hybridization probe pair according to claim 13, wherein one probe of the probe pair comprises SEQ ID NO:5 or the complementary sequence thereof.

16. The hybridization probe pair according to claim 13, wherein one probe of the probe pair comprises SEQ ID NO:6 or the complementary sequence thereof.

17. The hybridization probe pair according to claim 13, wherein one probe in the probe pair comprises SEQ ID NO:4 and the other probe comprises SEQ ID NO:5, or one probe in the probe pair comprises the complementary sequence of SEQ ID NO:4 and the other probe comprises the complementary sequence of SEQ ID NO:5.

18. The hybridization probe pair according to claim 13, wherein one probe in the probe pair comprises SEQ ID NO:4 and the other probe comprises SEQ ID NO:6, or one probe in the probe pair comprises the complementary sequence of SEQ ID NO:4 and the other probe comprises the complementary sequence of SEQ ID NO:6.

19. A hybridization probe comprising SEQ ID NO:4 or the complementary sequence thereof.

20. A hybridization probe comprising SEQ ID NO:5 or the complementary sequence thereof.

21. A kit for detecting *M. tuberculosis*, comprising:
at least one primer pair suitable for amplifying a DNA segment from SEQ ID NO:1, wherein the DNA segment comprises position −215 in the 5' to 3' direction of reading upstream of the translation start codon GTG of the narGHJI nitrate reductase operon, or
at least one hybridization probe or a hybridization probe pair suitable for detecting the polymorphism specific for *M. tuberculosis* located in position −215 in the 5' to 3' direction of reading upstream of the translation start codon GTG of the narGHJI nitrate reductase operon, wherein the polymorphism specific for *M. tuberculosis* in position −215 is thymine (T).

22. The kit according to claim 21, wherein one primer of the primer pair comprises SEQ ID NO:2 and the other primer comprises SEQ ID NO:3.

23. The kit according to claim 21, wherein (a) one probe in the hybridization probe pair comprises SEQ ID NO:4 and the other probe in the probe pair comprises SEQ ID NO:5;

(b) one probe in the hybridization probe pair comprises the complementary sequence of SEQ ID NO:4 and the other probe in the probe pair comprises the complementary sequence of SEQ ID NO:5;

(c) one probe in the hybridization probe pair comprises SEQ ID NO:4 and the other probe in the probe pair comprises SEQ ID NO:6; or (d) one probe in the hybridization probe pair comprises the complementary sequence of SEQ ID NO:4 and the other probe in the probe pair comprises the complementary sequence of SEQ ID NO:6.

24. The kit according to claim 23, wherein one primer of the primer pair comprises SEQ ID NO:2 and the other primer of the primer pair comprises SEQ ID NO:3.

25. The kit according to claim 21 or claim 22, further comprising reagents or auxiliary agents for carrying out a nucleic acid amplification or detection reaction.

26. A method for determining the presence or absence of *Mycobacterium tuberculosis* (*M. tuberculosis*) in clinical material, comprising a) extracting microbial DNA from clinical material, b) performing nucleic acid amplification in the presence of the extracted DNA and a primer pair suitable for amplifying a DNA fragment of the promoter region of the narGHJI nitrate reductase operon of mycobacteria containing the nucleotide located in position −215 of the promoter region, in the 5' to 3' direction of reading, upstream of the translation start codon GTG of the narGHJI mitrate reductase operon, and c) determining in the amplification product of step (b), the presence or absence of the polymorphism specific for *M. tuberculosis* in position −215 by way of melting curve analysis with at least one hybridization probe that comprises the nucleotide sequence selected from the group consisting of SEQ ID NO:5, the complementary sequence to SEQ ID NO:5, SEQ ID NO:6, and the complementary sequence to SEQ ID NO:6, wherein the presence of the polymorphism specific for *M. tuberculosis* in position −215 indicates the presence of *M. tuberculosis* in the clinical material, and the absence of the polymorphism specific for *M. tuberculosis* in position −215 indicates the absence of *M. tuberculosis* in the clinical material, and wherein the polymorphism specific for *M. tuberculosis* in position −215 is thymine (T).

27. The method according to claim 26, wherein step b) is carried out by means of a primer pair having one primer that comprises SEQ ID NO:2 and the other primer comprises SEQ ID NO:3.

28. The method according to claim 26 or claim 27, wherein step c) is carried out with at least one pair of labeled hybridization probes, and wherein one probe of the pair comprises SEQ ID NO:4 and the other probe comprises SEQ ID NO:5, one probe of the pair comprises the complementary sequence of SEQ ID NO:4 and the other probe comprises the complementary sequence of SEQ ID NO:5, one probe of the pair comprises SEQ ID NO:4 and the other probe comprises SEQ ID NO:6, or one probe of the pair comprises the complementary sequence of SEQ ID NO:4 and the other probe comprises the complementary sequence of SEQ ID NO:6.

29. The method according to claim 26 or claim 27, wherein step (b) is carried out by polymerase chain reaction (PCR).

30. The method according to claim 26 or claim 27, wherein step (c) is carried out during or after step (b).

31. The method according to claim 26 or claim 27, wherein step (c) is carried out via real time PCR.

32. The method according to claim 26 or claim 27, wherein step (c) is carried out by fluorescence detection, and the labeled hybridization probe pairs are formed as fluorescence resonance energy transfer (FRET) pair.

33. The method according to claim 26 or claim 27, wherein the clinical material is selected from the group of clinical samples consisting of saliva, bronchial lavage, gastric juice, urine, faeces, liquor, bone marrow, blood and biopsies.

34. An oligonucleotide which hybridizes specifically with an *M. tuberculosis*-specific promoter region of the narGHJI nitrate reductase operon, comprising SEQ ID NO:5 or the complementary sequence thereof.

35. An oligonucleotide which hybridizes specifically with an *M. tuberculosis*-specific promoter region of the narGHJI nitrate reductase operon, comprising the nucleotide sequence SEQ ID NO:6 or the complementary sequence thereof.

36. An oligonucleotide pair, wherein one oligonucleotide in the pair comprises SEQ ID NO:4 and the other oligonucleotide comprises SEQ ID NO:5, or one oligonucleotide in the pair comprises the complementary sequence of SEQ ID NO:4 and the other oligonucleotide comprises the complementary sequence of SEQ ID NO:5.

37. An oligonucleotide pair, wherein one oligonucleotide in the pair comprises SEQ ID NO:4 and the other comprises SEQ ID NO:6, or one oligonucleotide in the pair comprises the complementary sequence of SEQ ID NO:4 and the other comprises the complementary sequence of SEQ ID NO:6.

38. A kit for detecting *Mycobacterium tuberculosis* comprising
- a) at least one primer pair, wherein one primer in the primer pair comprises SEQ ID NO:2, and the other primer comprises SEQ ID NO:3 and
- b) at least one hybridization probe pair, wherein one probe in the probe pair comprises SEQ ID NO:4 and the other probe comprises SEQ ID NO:5, one probe in the probe pair comprises the complementary sequence of SEQ ID NO:4 and the other probe comprises the complementary sequence of SEQ ID NO:5, one probe in the probe pair comprises SEQ ID NO:4 and the other probe comprises SEQ ID NO:6, or one probe in the probe pair comprises the complementary sequence of SEQ ID NO:4 and the other probe comprises the complementary sequence of SEQ ID NO:6.

39. The method of claim 26, wherein the at least one hybridization probe in step (c) comprises SEQ ID NO:6 or the complementary sequence thereof.

40. The method according to claim 1, wherein one primer of the primer pair of step (a) comprises SEQ ID NO:2.

41. The method according to claim 1, wherein one primer of the primer pair of step (a) comprises SEQ ID NO:3.

42. The method according to claim 1, wherein one primer of the primer pair of step (a) comprises SEQ ID NO:2 and the other primer comprises SEQ ID NO:3.

43. The hybridization probe of claim 12, wherein the hybridization probe hybridizes to (a) a region of SEQ ID NO:7 or SEQ ID NO:8 that encompasses position −215, or (b) the complement of the region of SEQ ID NO:7 or SEQ ID NO:8 that encompasses position −215.

44. The hybridization probe pair of claim 13, wherein one of the hybridization probe pair hybridizes to (a) a region of SEQ ID NO:7 or SEQ ID NO:8 that encompasses position −215, or (b) the complement of the region of SEQ ID NO:7 or SEQ ID NO:8 that encompasses position −215.

45. A hybridization probe comprising SEQ ID NO:6 or the complementary sequence thereof.

46. The hybridization probe of claim 19, wherein the probe is at most 50 nucleotides in length.

47. The hybridization probe of claim 20, wherein the probe is at most 50 nucleotides in length.

48. The hybridization probe of claim 45, wherein the probe is at most 50 nucleotides in length.

* * * * *

SEQUENCE LISTING

<160> NUMBER OF SEQ ID NOS: 9

<210> SEQ ID NO 1
<211> LENGTH: 3002
<212> TYPE: DNA
<213> ORGANISM: Mycobacterium tuberculosis

<400> SEQUENCE: 1

```
ctcgggtgtc aagttgacgc cggcgattac cgctgtctac ctcgtcggcg ttcggcggtt      60
gcatgcggcc gcattttcgg tggtcgtgtt ccttgccacc gtcggcgtgt cgctactggt     120
cgtcggcgat gaagcccgct actacttcac cgacctgttg ggcgacgcag gccgggttgg     180
gcccatcgcc acctccttca atcaatcctg gcgcggcgcg atttcccgga ttctcggtca     240
cgacgccggt tttggtccgc tggttctggc tgcgatcgcc agtacggcgg tattggccat     300
cctggcctgg cgtgcgctcg acaggtccga tcggctgggc aaactattgg tggtcgagtt     360
gttcggcctg ctgctctcgc cgatctcctg gactcaccac tgggtgtggc tagtgccgct     420
gatgatctgg ctgattgacg ggccagcgcg tgagcgcccg ggcgcccgga ttttgggctg     480
gggctggttg gtgttgacca tcgtcggcgt gccgtggttg ctgagctttg ctcaaccgag     540
catctggcaa atcggccggc cgtggtattt ggcctgggcc ggtctggtct acgtggtggc     600
gacgctggcg accttgggct ggatcgccgc ctccgagcgt tacgtgcgca ttcggccgcg     660
gcgcatggcc aattaggccc caaacattgc gtcgatatcg tgcgccatcg caatgtcgtt     720
ttccgtgata ccacctaccg catgcgtaac cagcgcgaaa gttactgttc gccaacggat     780
atcgatgtcc ggatgatgat ttacctcctc ggctcgctcg gccaccccggc gtacggcgtc     840 gataccggcc ataaacgtcg gaaacttgat tgacctacgc aggacaccac cggcgcgctg     900
ccagccgttg aggtcgtgca gtgcggcgtc gacctgctca tccgttaaca cagccatacc     960
tcgacggtat accgtcacag gtcatgctga atcagatcgt ggttgccgga gccatcgtcc    1020
gcggttgcac ggtcttggtg gcgcaacgcg ttcggccacc ggagttggcg ggtcgttggg    1080
aacttcccgg cggtaaggtc gccgccggcg aaaccgagcg cgccgcgctg gcccgagagc    1140
tcgccgaaga actgggactc gaggtcgccg acctcgcggt gggcgaccgt gtgggcgacg    1200
atattgcgtt gaacggcacg acgacgctgc gggcctatcg cgtgcatctg cttgcgcgcg    1260
aaccgcgtgc gcgtgaccac cgggcgctgt gctgggtgac ggcggccgaa ctgcacgatg    1320
```

-continued

```
tcgactgggt accagccgac cgcggctgga ttgcggacct ggcgcgaacc ctcaacgggt    1380
ccgccgcaga tgtccaccgt cgctgttagg aaaccgacgg tgtggttgac ggtggccgcc    1440
gtcaacttgg ttagaacaac gtgacaaaac gttaacttgg gttttgcatgc ccgtagcgat   1500 tacgatggtt ttctggacgc gtggcgacaa cttccgggca ggacgctgac gcccatccat    1560
cgagataccc gatgttgacg agaggggtcc ccgacccggc ggaccggggc ttgacgggcg    1620
caatgcggcg cggccggcca gcccgtaacg tccagcgagt cgtcgcgc gccgacggcc       1680 cggccccaca ccgctcatga cgaggagggt catcccgtga ccgttacacc tcacgtcggt    1740
ggaccgctcg aagagctgct ggagcgcagc gggcgcttct tcaccccagg tgagttctcg    1800
gccgacctgc gcaccgtaac ccggcgcggc ggccgcgaag gtgacgtgtt ctaccgcgat    1860
cggtggagtc acgacaaagt ggtccgatcc acgcacggag tcaactgcac cggatcctgc    1920
tcatggaaga tctacgtcaa agacgggatc atcacctggg aaacccagca gaccgactac    1980
ccgtcggtgg gccggaccg gcccgaatac gagccacgag gttgtccccg tggcgcgtcg     2040
ttctcctggt acagctattc gccgacgcgg gtgcgctatc cgtatgcccg gggcgtgctg    2100
gttgagatgt accgggaagc caagaccccgc ctgggcgacc cggtgctggc gtgggccgac   2160
attcaggcgg atcccgagcg cagacgccgc tatcaacagg cccgcggcaa gggtgggctg    2220
gtccgggtga gctgggccga ggccagcgag atggtggccg ccgcccacgt gcacaccatc    2280
aagacatacg gcccggaccg ggtcgccggc ttctcgccga ttccggcgat gtcaatggtc    2340
agccatgccg cggggtcccg gttcgtggag ctgatcggcg gcgtgatgac gtcgttctac    2400
gactggtacg ccgacttgcc ggtggcctcg ccgcaggtgt tcggcgacca gaccgacgtg    2460
cccgaatccg gcgactggtg ggatgcgtcg tatttggtca tgtggggctc caacgtcccg    2520
atcacccgga cgcccgacgc acattggatg gcggaggccc gttaccgcgg cgctaaagtc    2580
gttgtcgtca gcccggacta cgccgacaac accaagttcg ccgacgagtg ggtgcggtgc    2640
gccgccggta ccgataccgc gctggcgatg gcgatgggcc acgtgatcct gtcggaatgt   2700
tacgtccgta accaggttcc gttctttgtc gactatgtgc gccgctacac cgacctgccg    2760
tttttgatca agttggaaaa gcggggcgac ctgctggttc ccggaaagtt cttgaccgcg    2820
gccgacattg gtgaagaaag tgagaacgcg gcgttcaaac ccgccctgct ggatgagctt    2880
acgaataccg ttgtcgtgcc gcagggctca ctgggattcc gtttcggtga ggacggtgtt    2940
gggaagtgga acctggacct gggttcggtg gtgccggcgc taagtgtgga gatggacaag    3000
gc                                                                   3002
```

<210> SEQ ID NO 2
<211> LENGTH: 19
<212> TYPE: DNA
<213> ORGANISM: Mycobacterium

<400> SEQUENCE: 2
aaccgacggt gtggttgac                                                 19

<210> SEQ ID NO 3
<211> LENGTH: 19
<212> TYPE: DNA
<213> ORGANISM: Mycobacterium

<400> SEQUENCE: 3
atctcgatgg atgggcgtc                                                 19

```
<210> SEQ ID NO 4
<211> LENGTH: 22
<212> TYPE: DNA
<213> ORGANISM: Mycobacterium

<400> SEQUENCE: 4
gtcgccacgc gtccagaaaa cc                                               22

<210> SEQ ID NO 5
<211> LENGTH: 18
<212> TYPE: DNA
<213> ORGANISM: Mycobacterium

<400> SEQUENCE: 5
cgtgatcgct acgggcat                                                    18

<210> SEQ ID NO 6
<211> LENGTH: 19
<212> TYPE: DNA
<213> ORGANISM: Mycobacterium

<400> SEQUENCE: 6
cgtaatcgct acgggcatg                                                   19

<210> SEQ ID NO 7
<211> LENGTH: 524
<212> TYPE: DNA
<213> ORGANISM: Mycobacterium tuberculosis

<400> SEQUENCE: 7
acgatattgc gttgaacggc acgacgacgc tgcgggccta tcgcgtgcat ctgcttggcg       60
gcgaaccgcg tgcgcgtgac caccgggcgc tgtgctgggt gacggcggcc gaactgcacg      120
atgtcgactg ggtaccagcc gaccgcggct ggattgcgga cctggcgcga accctcaacg      180
ggtccgccgc agatgtccac cgtcgctgtt aggaaaccga cggtgtggtt gacggtggcc      240
gccgtcaact tggttagaac aacgtgacaa acgttaact tgggtttgca tgcccgtagc       300
gattacgatg gttttctgga cgcgtggcga caacttccgg gcaggacgct gacgcccatc      360
catcgagata cccgatgttg acgagagggg tccccgaccc ggcggaccgg ggcttgacgg      420
gcgcaatgcg gcgcggccgg ccagcccgta acgtccagcg agtgcggtcg cgcgccgacg      480 gccccggcccc acaccgctca tgacgaggag gtcatcccgt gacc                     524

<210> SEQ ID NO 8
<211> LENGTH: 524
<212> TYPE: DNA
<213> ORGANISM: Mycobacterium bovis

<400> SEQUENCE: 8
acgatattgc gttgaacggc acgacgacgc tgcgggccta tcgcgtgcat ctgcttggcg       60
gcgaaccgcg tgcgcgtgac caccgggcgc tgtgctgggt gacggcggcc gaactgcacg      120
atgtcgactg ggtaccagcc gaccgcggct ggattgcgga cctggcgcga accctcaacg      180
ggtccgccgc agatgtccac cgtcgctgtt aggaaaccga cggtgtggtt gacggtggcc      240
gccgtcaact tggttagaac aacgtgacaa acgttaact tgggtttgca tgcccgtagc       300
gatcacgatg gttttctgga cgcgtggcga caacttccgg gcaggacgct gacgcccatc      360
catcgagata cccgatgttg acgagagggg tccccgaccc ggcggaccgg ggcttgacgg      420
gcgcaatgcg gcgcggccgg ccagcccgta acgtccagcg agtgcggtcg cgcgccgacg      480
```

-continued

```
gcccggcccc acaccgctca tgacgaggag gtcatcccgt gacc                  524

<210> SEQ ID NO 9
<211> LENGTH: 524
<212> TYPE: DNA
<213> ORGANISM: Mycobacterium bovis BCG

<400> SEQUENCE: 9
acgatattgc gttgaacggc acgacgacgc tgcgggccta tcgcgtgcat ctgcttggcg    60
gcgaaccgcg tgcgcgtgac caccgggcgc tgtgctgggt gacggcggcc gaactgcacg   120
atgtcgactg ggtaccagcc gaccgcggct ggattgcgga cctggcgcga accctcaacg   180
ggtccgccgc agatgtccac cgtcgctgtt aggaaaccga cggtgtggtt gacggtggcc   240
gccgtcaact tggttagaac aacgtgacaa aacgttaact tgggtttgca tgcccgtagc   300
gatcacgatg gttttctgga cgcgtggcga caacttccgg gcaggacgct gacgcccatc   360
catcgagata cccgatgttg acgagagggg tccccgaccc ggcggaccgg ggcttgacgg   420
gcgcaatgcg gcgcggccgg ccagcccgta acgtccagcg agtgcggtcg cgcgccgacg   480
gcccggcccc acaccgctca tgacgaggag gtcatcccgt gacc                  524
```